(12) United States Patent
Mütze et al.

(10) Patent No.: US 9,069,093 B2
(45) Date of Patent: Jun. 30, 2015

(54) METHOD AND APPARATUS FOR DETERMINING THE LOCAL SPATIAL EXTENT OF THE PHASE OF VALUABLE MINERAL IN A ROCK

(75) Inventors: Thomas Mütze, Freiberg (DE); Silke Röntzsch, Großröhrsdorf (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 385 days.

(21) Appl. No.: 13/702,264

(22) PCT Filed: Mar. 29, 2011

(86) PCT No.: PCT/EP2011/054771
§ 371 (c)(1),
(2), (4) Date: Dec. 5, 2012

(87) PCT Pub. No.: WO2011/154170
PCT Pub. Date: Dec. 15, 2011

(65) Prior Publication Data
US 2013/0081458 A1 Apr. 4, 2013

(30) Foreign Application Priority Data
Jun. 7, 2010 (EP) .................................... 10165045

(51) Int. Cl.
*E21B 47/12* (2012.01)
*G01V 9/00* (2006.01)
(Continued)

(52) U.S. Cl.
CPC .............. *G01V 9/007* (2013.01); *E21B 49/005* (2013.01); *G01N 15/0255* (2013.01); *G01N 2015/0288* (2013.01)

(58) Field of Classification Search
CPC ....... E21B 47/00; E21B 47/011; G01V 11/00; G01V 1/40
USPC ...................................................... 73/152.02
See application file for complete search history.

(56) References Cited

U.S. PATENT DOCUMENTS

| | | | |
|---|---|---|---|
| 2,082,329 A | 6/1937 | Foran et al. | 175/48 |
| 2,167,393 A | 7/1939 | Muncy | 175/49 |

(Continued)

FOREIGN PATENT DOCUMENTS

| | | | |
|---|---|---|---|
| CN | 1643233 A | 7/2005 | E21B 21/08 |
| CN | 2919251 Y | 7/2007 | G01N 15/00 |

(Continued)

OTHER PUBLICATIONS

Australian Office Action, Application No. 2011264086, 3 pages, Oct. 1, 2013.

(Continued)

*Primary Examiner* — Hezron E Williams
*Assistant Examiner* — Rodney T Frank
(74) *Attorney, Agent, or Firm* — Slayden Grubert Beard PLLC

(57) ABSTRACT

A method and an apparatus are provided for determining a local mineral grain size of a valuable mineral in a rock of a deposit or an occurrence, where the rock comprises at least one other mineral, and wherein the valuable mineral has a higher density than the at least one other mineral. The method may include: performing a drilling operation using a drill in the rock, with cuttings being produced, forming an aerosol comprising the cuttings and a gas stream, transferring the aerosol from the drill to at least one air classifier, performing stream classification, wherein at least two fractions comprising in each case particles of the cuttings that sink at the same speed are formed, and determining a property of at least one of the fractions, which fraction is used as a measure for the local mineral grain size of the valuable mineral in the rock.

17 Claims, 2 Drawing Sheets

(51) Int. Cl.
  *E21B 49/00* (2006.01)
  *G01N 15/02* (2006.01)

(56) References Cited

U.S. PATENT DOCUMENTS

| | | | | |
|---|---|---|---|---|
| 3,528,514 | A | | 9/1970 | Sandvig ........................ 175/49 |
| 3,645,131 | A | | 2/1972 | Turner et al. ............... 73/152.04 |
| 3,887,020 | A | | 6/1975 | Chaffin ....................... 175/206 |
| 3,968,845 | A | * | 7/1976 | Chaffin ........................ 175/60 |
| 4,098,698 | A | | 7/1978 | Lamothe ...................... 210/309 |
| 4,633,712 | A | | 1/1987 | Scieszka ....................... 73/866 |
| 4,712,424 | A | * | 12/1987 | Herron ..................... 73/152.14 |
| 4,722,220 | A | * | 2/1988 | Herron ..................... 73/152.14 |
| 6,301,953 | B1 | | 10/2001 | Zamfes ............................ 73/38 |
| 6,453,727 | B1 | | 9/2002 | Lenormand et al. ............ 73/38 |
| 6,904,981 | B2 | | 6/2005 | Van Riet et al. ................. 175/66 |
| 7,980,329 | B2 | | 7/2011 | Spiecker et al. .............. 175/206 |
| 8,042,753 | B2 | | 10/2011 | Yamaguchi et al. ..... 241/101.74 |
| 8,240,480 | B2 | | 8/2012 | Shaw et al. ....................... 209/11 |
| 2003/0182997 | A1 | | 10/2003 | Williams .................... 73/152.23 |
| 2005/0087018 | A1 | | 4/2005 | Zamfes ........................... 73/601 |
| 2006/0107772 | A1 | | 5/2006 | Shinn, II et al. ............ 73/864.43 |
| 2007/0137293 | A1 | | 6/2007 | Pop et al. .................... 73/152.23 |
| 2008/0202811 | A1 | | 8/2008 | Zamfes .......................... 175/46 |
| 2009/0302141 | A1 | | 12/2009 | Yamaguchi et al. ............ 241/33 |
| 2010/0000055 | A1 | | 1/2010 | Poulakis ..................... 24/30.5 R |

FOREIGN PATENT DOCUMENTS

| | | | | |
|---|---|---|---|---|
| CN | 101395336 | A | 3/2009 | ............. E21B 21/01 |
| CN | 101553323 | A | 10/2009 | ............. B06C 5/342 |
| DE | 10008106 | A1 | 8/2001 | ............. E21B 49/00 |
| DE | 10116363 | A1 | 10/2002 | ............. E21B 47/00 |
| RU | 2268364 | C2 | 1/2006 | ............. E21B 49/00 |
| WO | 2009/105469 | A2 | 8/2009 | ............. E21B 43/34 |
| WO | 2010/000055 | A1 | 1/2010 | ............. E21B 21/06 |
| WO | 2011/154168 | A1 | 12/2011 | ............. E21B 21/06 |
| WO | 2011/154169 | A1 | 12/2011 | ............. E21B 21/07 |
| WO | 2011/154170 | A1 | 12/2011 | ............. E21B 21/06 |

OTHER PUBLICATIONS

Australian Office Action, Application No. 2011264084, 3 pages, Mar. 11, 2014.

Australian Office Action, Application No. 2011264085, 2 pages, Oct. 13, 2014.

Holmes, Ralph J., "Correct Sampling and Measurement—the Foundation of Accurate Metallurgical Accounting," Chemometrics and Intelligent Laboratory Systems, vol. 74, Elsevier Science Publishers, 14 pages, Mar. 12, 2004.

International Search Report and Written Opinion, Application No. PCT/EP2011/054767, 13 pages, May 11, 2011.

International Search Report and Written Opinion, Application No. PCT/EP2011/054769, 13 pages, May 11, 2011.

International Search Report and Written Opinion, Application No. PCT/EP2011/054771, 24 pages, Jul. 4, 2011.

Australian Office Action, Application No. 2011264085, 3 pages, Jun. 2, 2014.

Chinese Office Action, Application No. 2011800283838, 12 pages, Jun. 30, 2014.

* cited by examiner

METHOD AND APPARATUS FOR DETERMINING THE LOCAL SPATIAL EXTENT OF THE PHASE OF VALUABLE MINERAL IN A ROCK

CROSS-REFERENCE TO RELATED APPLICATIONS

This application is a U.S. National Stage Application of International Application No. PCT/EP2011/054771 filed Mar. 29, 2011, which designates the United States of America, and claims priority to EP Patent Application No. 10165045.5 filed Jun. 7, 2010 The contents of which are hereby incorporated by reference in their entirety.

TECHNICAL FIELD

The disclosure relates to a method and an apparatus for determining a local mineral grain size of a valuable mineral in a rock of a deposit or an occurrence, wherein the rock includes at least one other mineral, and wherein the valuable mineral has a higher density than the at least one other mineral.

BACKGROUND

"Mineral grain size" of the valuable mineral is to be understood as referring not to the grain size of the crystallites of said mineral, but to the local spatial extent of the phase of valuable material in the rock.

The mineral grain size and distribution of minerals in a rock has hitherto been time-consumingly determined by taking rock samples at different locations in a deposit or an occurrence and analyzing them. For this purpose, for example, approximately fist-sized lumps of rock are collected and/or exploratory drilling is carried out in a coarse grid pattern in order to obtain evaluatable cores. These rock samples are analyzed in the laboratory in respect of their mineralogical and chemical composition. While the chemical analysis essentially determines the nature and extent of the constituent elements, in the mineralogical analysis the nature and extent of the constituent minerals as well as their spatial arrangement is ascertained. To determine the spatial arrangement of the minerals, the rock samples are ground in the direction of defined spatial axes. By means of optical analysis of the thin or polished section obtained, e.g. under a microscope, the spatial arrangement and distribution of the minerals in the rock can be identified. A spatially widely distributed arrangement of the minerals is associated with a small mineral grain size, while clustering of minerals at particular locations is associated with a larger mineral grain size.

In respect of the structure of a deposit or an occurrence or more specifically the spatial size distribution of the mineral grains in the deposit or occurrence, only a small amount of information can be provided in this way, and this only after a considerable time delay.

Because of this paucity of information, deposit modeling, i.e. creating a model of the deposit or occurrence comprising the three-dimensional plotting of rock layers or rock formations having different grain sizes of the valuable mineral, is virtually impossible. Extraction geared to the locally present rock, i.e. its valuable mineral content and the mineral grain size thereof, and selective utilization is therefore possible only to a limited extent.

Depending on the grain size of the minerals, different size reduction ratios may be required in order to be able to expose the valuable mineral and efficiently separate it from the entire extracted material throughput. Thus, to expose the valuable mineral, a rock including valuable minerals having a high mineral grain size needs to be less intensively comminuted than a rock including valuable minerals having a lower mineral grain size.

The extracted rock has hitherto been comminuted to an average mineral grain size, wherein a first portion of the rock including a valuable mineral having a high mineral grain size is unnecessarily finely comminuted, and a second portion of the rock including a valuable mineral having a lower mineral grain size is insufficiently comminuted. The unnecessarily fine comminution of the first portion of the rock results in an unnecessarily high energy consumption for the comminution process. On the other hand, the insufficient comminution of the second portion of the rock results in inadequate exposing and consequently inadequate separability of the valuable mineral and ineffective exploitation of the deposit.

WO 2010/000055 A1 discloses a method and an apparatus for in particular continuous on-site analysis of drill cuttings from drilling mud. A drill cutting sample which is representative of the drilled rock formation is taken and analyzed in respect of the type of rock and the chemical composition. If necessary, drilling parameters including drilling depth, gamma ray emissions and/or other parameters are logged and correlated with the sample analysis results.

SUMMARY

In one embodiment, a method is provided for determining a local mineral grain size of a valuable mineral in a rock of a deposit or occurrence, wherein the rock comprises at least one other mineral, and wherein the valuable mineral has a higher density than the at least one other mineral, the method comprising: performing a drilling operation in the rock using a drill, wherein drill cuttings are produced, forming an aerosol comprising the drill cuttings and a gas stream, conveying the aerosol from the drill to at least one air classifier, performing hydraulic classification, wherein at least two fractions each comprising equal-settling particles of the drill cuttings are formed, and determining a property of at least one of the fractions which is used as a measure for the local mineral grain size of the valuable mineral in the rock.

In a further embodiment, the property is determined by performing particle size analysis on the equal-settling particles of the fractions, wherein at least one of the fractions includes two particle fractions having different average particle sizes which are separated from one another by a gap grading, and wherein the particle sizes d of a first particle fraction are used as a measure for the local mineral grain size of the valuable mineral in the rock. In a further embodiment, in the case that particle size analyses of at least two fractions each show a gap grading, the first particle fraction is used as a measure for the local mineral grain size of the valuable mineral in the rock, which particle fraction comes from the fraction having the largest gap grading. In a further embodiment, the local mineral grain size of an ore mineral is determined. In a further embodiment, particle size analysis is performed automatically by optical analysis. In a further embodiment, particle size analysis of the equal-settling particles of the fractions takes place continuously during the fall thereof. In a further embodiment, during the drilling operation, a depth of a drill bit of the drill and/or position data relating to the position of the drill bit in the deposit or occurrence are recorded and logically linked with the measure associated with this location, and that a three-dimensional mineral grain size distribution of the valuable mineral in the deposit or occurrence is determined therefrom. In a further embodiment, on the drill at least one predefined drilling parameter and at least one measured value characterizing a current drilling behavior of the drill are recorded, a dependence of the at least one measured value on the at least one drilling parameter is computationally eliminated, and that at least one resulting rock texture dependent characteristic value is used as another measure for determining the local mineral grain size of the valuable mineral. In a further embodiment, the at least one drilling parameter is constituted by a pressure of the drill bit of the drill and/or a rotational speed of the drill bit and/or a flow rate of the gas stream for forming the aerosol and/or an impact frequency of the drill bit and/or a previous period of use of the drill bit and/or material or geometry data of the drill bit. In a further embodiment, the at least one measured value characterizing the current drilling behavior is selected from the group of measured values comprising the drilling rate, a resulting torque on the top drive of the drill bit, a gas pressure of the gas stream for forming the aerosol, an energy input to the drill, and a vibration behavior of a drill pipe of the drill.

In another embodiment, an apparatus is provided for performing any of the methods disclosed above, the apparatus comprising: at least one drill, at least one unit for providing the gas stream for forming the aerosol, which unit is connected via at least one gas line to the at least one drill, at least one air classifier for each drill, which air classifier is connected to the at least one drill via at least one aerosol line, at least one device for performing the determination of the property of the fractions, and at least one processor unit connected to the at least one device by a data link and which is used to record the property and correlate it with the local mineral grain size of the valuable mineral in the rock.

In a further embodiment, the at least one device is configured to perform particle size analysis, and wherein the at least one device or the at least one processor unit is used to correlate the first particle fraction with the local mineral grain size of the valuable mineral in the rock. In a further embodiment, the at least one processor unit is additionally used to record, at the drill, the at least one drilling parameter or the at least one measured value characterizing the current drilling behavior of the drill. In a further embodiment, the at least one processor unit is additionally configured to computationally eliminate a dependence of the at least one measured value characterizing the current drilling behavior of the drill on the at least one drilling parameter and calculate the at least one rock texture dependent characteristic value which constitutes another measure for the local mineral grain size of the valuable mineral and/or a hardness of the rock. In a further embodiment, the at least one processor unit is additionally configured to determine the local mineral grain size of the valuable mineral on the basis of the measure and the additional measure. In a further embodiment, the at least one air classifier and the at least one device, in particular for performing particle size analysis, are disposed in immediate proximity to the drill, in particular on the drill. In a further embodiment, the apparatus includes at least one structure-borne noise sensor provided on the at least one drill for detecting a vibration behavior of the drill pipe of the drill.

BRIEF DESCRIPTION OF THE DRAWINGS

Example embodiments will be explained in more detail below with reference to figures, in which.

DETAILED DESCRIPTION

Figure 1:
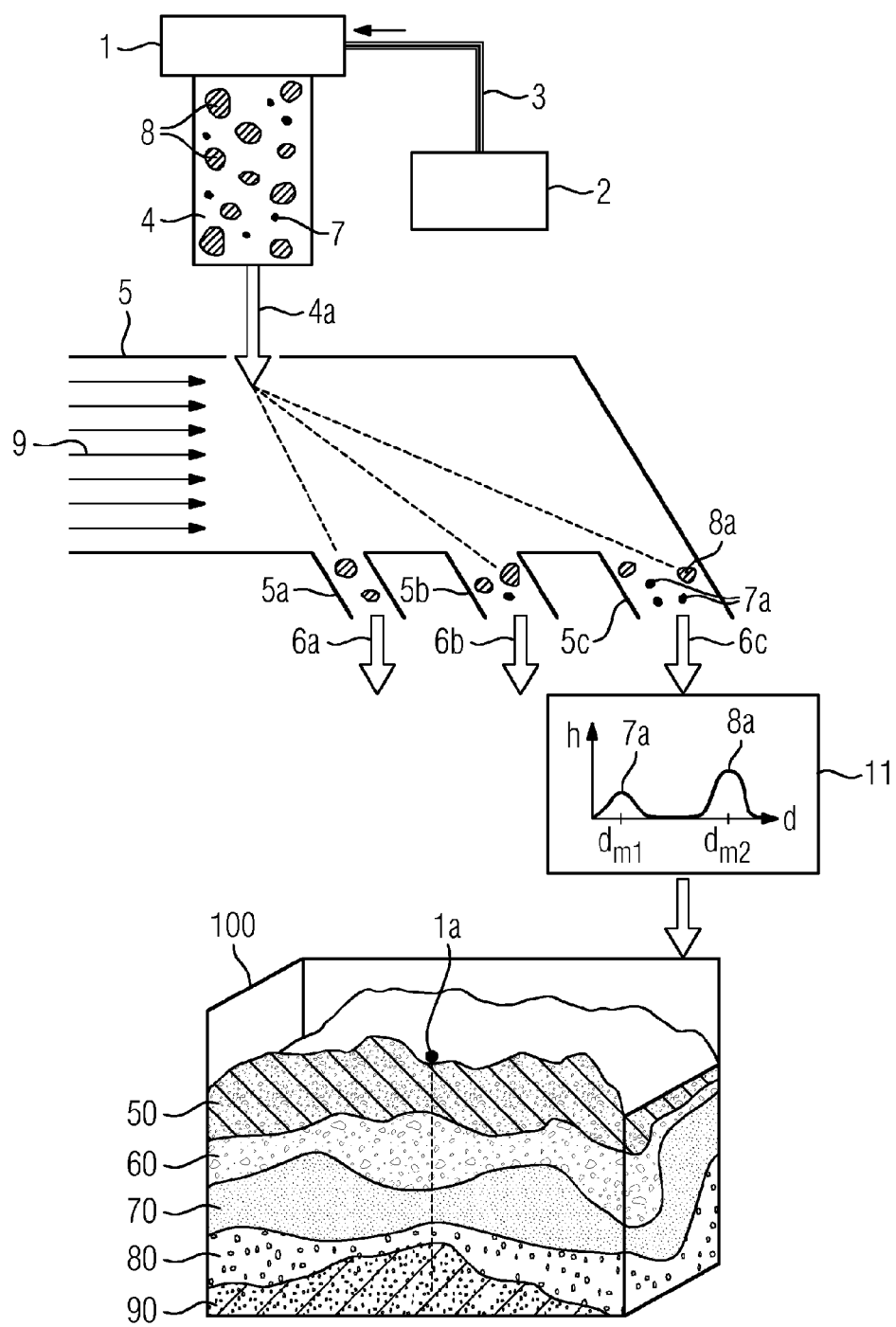
FIG. 1 schematically illustrates a method sequence, according to an example embodiment, FIG. 2 schematically illustrates an apparatus for performing the method, according to an example embodiment, and FIG. 3 schematically illustrates the main data and material flows for an example embodiment of the method.

Some embodiments provide a method and an apparatus which enables a local mineral grain size of a valuable mineral in the rock of a deposit or an occurrence to be determined quickly and in high resolution.

This object is achieved by a method for determining a local mineral grain size of a valuable mineral in a rock of a deposit or an occurrence, wherein the rock includes at least one other mineral, and wherein the valuable mineral has a higher density than the at least one other mineral, comprising the following steps:

performing a drilling operation in the rock using a drill, wherein drill cuttings are produced, forming an aerosol comprising the drill cuttings and a gas stream, conveying the aerosol from the drill to at least one air classifier, performing hydraulic classification, wherein at least two fractions each comprising equal-settling particles of the drill cuttings are formed, determining a property of at least one of the fractions which is used a measure for the local mineral grain size of the valuable mineral in the rock.

Other embodiments provide an apparatus for performing the disclosed method, which apparatus may include:

at least one drill, at least one unit for providing the gas stream, which unit is connected to the at least one drill via at least one gas line, at least one air classifier for each drill, which air classifier is connected to the respective drill via at least one aerosol line, at least one device for performing the determination of a property of at least one of the fractions, and, connected via a data link to the at least one device, at least one processor unit for recording the property and correlating it with the local mineral grain size of the valuable mineral in the rock.

Certain embodiments are based on the insight that the properties of drill cuttings produced by a drill during a drilling operation are directly related to the mineral grain size of the minerals that are present in the drilled rock. Selective evaluation of the properties of a hydraulically classified fraction of the drill cuttings surprisingly allows sufficiently accurate inferences to be drawn concerning the mineral grain size of the valuable mineral present in the drilled rock.

The method and the apparatus allow particularly rapid and sufficiently accurate determining of the mineral grain size of a valuable mineral in a rock. This determining takes place during the drilling process, so that the data is available promptly and on a depth-dependent basis for each hole. Instead of evaluating the cores obtained from core drilling to determine the respective rock structure, the drill cuttings can now be simply analyzed while a deposit is being prospected. The number of holes can be significantly increased, as time-consuming laboratory analyses of cores are no longer required. In particular, drilling to make blast holes, which are placed in a tighter grid pattern than exploratory drill holes, can also be used for determining the respective rock structure. Blast holes are typically sunk at a horizontal spacing of 2 to 5 m, enabling data with a vertical resolution in the decimeter range to be provided. This allows particularly quick and precise deposit modeling and consequently particularly efficient exploitation of the deposit.

In a preferred embodiment of the method, the property is determined by performing particle size analysis on the equal-settling particles of the fractions, wherein at least in one of the fractions two particle fractions having different average particle sizes are obtained which are separated from one another by a gap grading, and wherein the particle sizes d of a first particle fraction are used as a measure for the local mineral grain size of the valuable mineral in the rock. Gap grading is here to be understood as meaning a region in which no particles are present in the particle size analysis for particular particle sizes.

In the case that particle size analyses of at least two fractions each show a gap grading, the first particle fraction coming from the fraction in which the gap grading is the greatest, i.e. the gap between the first and the second particle fraction is the widest, is used as a measure for the local mineral grain size of the valuable mineral in the rock.

A particle size distribution in drill cuttings produced by a drill during a drilling operation is directly related to the mineral grain size of the minerals present in the drilled rock. Selective evaluation of the particle size distribution of a hydraulically classified fraction of the drill cuttings surprisingly allows sufficiently accurate inferences to be drawn concerning the mineral grain sizes of the valuable mineral that are present in the drilled rock.

The device for performing the determination of a property of the fractions is consequently preferably configured to perform particle size analysis, wherein the device and/or the at least one processor unit is configured to record the particle sizes of the first particle fraction and to correlate them with the local mineral grain size of the valuable mineral in the rock.

In general it is currently considered necessary for the method that the valuable mineral in the rock is at least 1.5 times denser than the at least one other mineral. In the case of smaller density differences, particle size analysis of one of the fractions obtained after hydraulic classification of drill cuttings will yield no particle fractions separated by a gap grading that are clearly distinguishable from one another, i.e. can be evaluated.

Because a certain time difference exists between the production of the drill cuttings and the evaluation of the particle size distribution of a hydraulically classified fraction of the drill cuttings, this must of course be taken into account in the modeling in order to be able to the assign the rock the correct valuable mineral grain size locally.

The local mineral grain size of a valuable mineral in the form of an ore mineral is preferably determined. The term "ore" denotes naturally occurring mineral aggregates of commercial interest from which one or more valuable materials can be extracted by processing. These are mainly minerals including varying amounts of metallic constituents, such as iron, copper, nickel, tin, zinc, silver, gold, etc.

In a particularly preferred embodiment of the method, particle size analysis of the hydraulically classified fractions takes place automatically, in particular by optical analysis preferably using laser diffraction. The particles of the fractions are optically recorded and measured. In particular, the particle size of the equal-settling particles of the fractions is analyzed continuously as they fall, e.g. directly at the corresponding outlet channel or discharge chute for the fraction at the air classifier. Thus, a particularly close time relationship exists between the result of the analysis and the drilling at a particular position in the rock, and this result can be easily computationally taken into account if the velocity of the drill cuttings in the aerosol is known.

During the drilling operation, in particular a depth of a drill bit of the drill and/or position data for the position of the drill bit in the deposit or the occurrence is detected and logically linked with the location-associated measure for the local mineral grain size in order to determine therefrom a three-dimensional mineral grain size distribution of the valuable mineral in the deposit or the occurrence. This procedure is also known as deposit modeling which has already been explained in the introduction. In order to determine the current position of the drill bit during drilling in the deposit or an occurrence as accurately as possible, in particular the depth of drilling and the drill hole inclination are measured and the position of the drilling site is acquired, preferably using a GPS unit.

At least one predefined drilling parameter and at least one measured value characterizing a current drilling behavior of the drill are preferably acquired at the drill. Any dependence of the at least one measured value on the at least one drilling parameter is then preferably computationally eliminated and at least one resulting rock texture dependent characteristic value is used as a further measure for determining the local mineral grain size of the valuable mineral. This improves the accuracy of the determination of the mineral grain sizes of the valuable mineral.

The at least one drilling parameter is constituted by, for example, a drill bit pressure of the drill, a drill bit speed, a drill bit material, a drill bit geometry, a flow rate of the gas stream, a length of use, i.e. a state of wear, of the drill bit, an impact frequency of the drill bit, and the like. Said impact frequency results, among other things, from the drill bit pressure and gas stream data.

The at least one measured value characterizing the current drilling behavior is selected in particular from the group of measured values comprising a drilling rate, a resulting torque on the top drive of the drill bit, a gas pressure of the gas stream, an energy input to the drill, a vibration behavior of the drill pipe of the drill and the like.

Thus, for example, the drilling rate is dependent among other things on the hardness and composition of the drilled rock, wherein a high hardness and/or an accumulation of hard minerals result in a reduction in the drilling rate. However, the drilling rate also depends on which drill and drilling tool is used. In particular, the type, geometry and state of wear of the drill bit are important. These drilling parameters must of course be taken into account for assessing the drilling rate.

The at least one processor unit of the apparatus is connected by a data link to the at least one device. This is to be understood as meaning either a cabled connection, but in particular a wireless radio connection. Wireless data transmission to the at least one processor unit enables said processor unit to be physically separated in a dust- and vibration-proof manner from the drilling operation.

The at least one processor unit of the apparatus is preferably also configured to record the at least one drilling parameter or the at least one measured value characterizing the current drilling behavior of the drill. For this purpose, sensors present on the drill can be used or additional sensors can be mounted to the drill.

The at least one processor unit is also advantageously configured to computationally eliminate a dependence of the at least one measured value characterizing a current drilling behavior of the drill on the at least one drilling parameter and to calculate the at least one rock texture dependent characteristic value which constitutes another measure for the local mineral grain size of the valuable mineral and/or a hardness of the rock. The computational elimination of the dependence of the drilling parameters may require a reasonable number or preliminary attempts in which the individual influencing variables are determined and correlated with one another. The database created in this way is stored on the at least one processor unit and is used to determine the characteristic value that is solely dependent on the rock texture.

Lastly, it is advantageous if the at least one processor unit is additionally configured to determine the local mineral grain size of the valuable mineral on the basis of the measure and of the additional measure, thereby once again improving the accuracy of the determined local value of the mineral grain size for the valuable mineral.

The at least one air classifier and the at least one device for determining a property of the selected fraction, in particular for performing particle size analysis, are preferably disposed in immediate proximity to the drill, in particular on the drill, thereby minimizing the time for transporting the drill cuttings from the point of origin to the air classifier, and the analysis time required. A cross-flow classifier is preferably used as the air classifier.

In a preferred embodiment of the apparatus, there is present on the at least one drill at least one structure-borne noise sensor for acquiring at least one measured value characterizing the current drilling behavior in the form of a vibration behavior of the drill pipe of the drill. Thus the properties of the rock, such as the hardness of the rock currently being drilled, can be inferred from the vibration of the drill pipe.

On the basis of the model determined in the at least one processor unit and the values additionally transmitted thereto, the working in the region of the deposit or occurrence can preferably be controlled using the at least one processor unit, particularly in respect of blasting, transportation and storage of the extracted rock and also of rock comminution. Thus, with knowledge of the model and therefore the local mineral grain size of the valuable mineral and possibly of the local hardness of the rock, the locally used quantity of explosive can be adjusted, and the extracted rock can be stored at different locations depending on quality or further comminuted in differing degrees in order to expose the valuable mineral.

Figure 2:
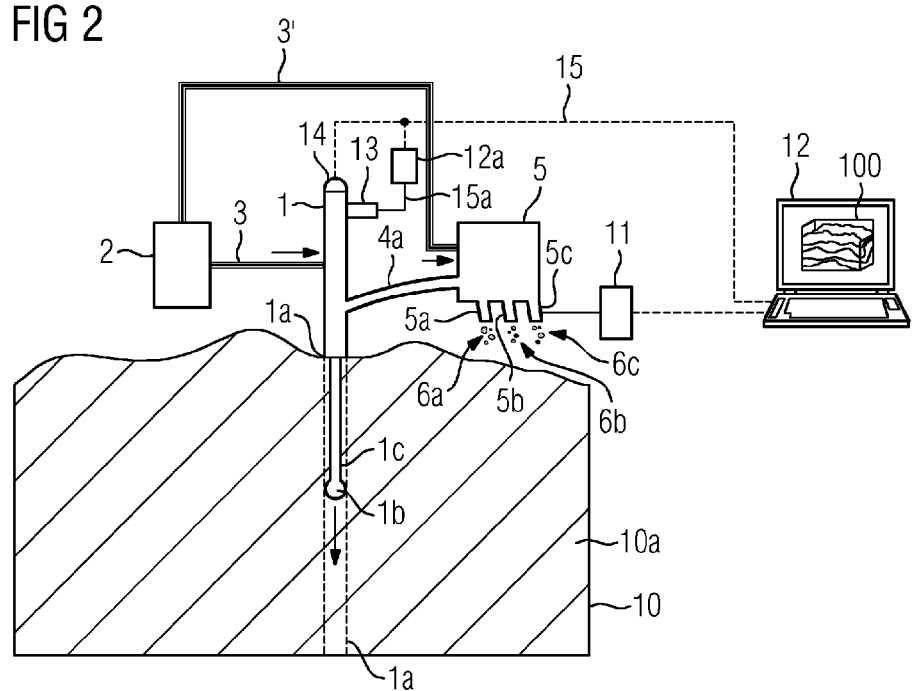

FIG. 1 schematically illustrates a method sequence for determining a local mineral grain size of a valuable mineral in a rock 10a of a deposit or occurrence 10 (cf. also FIG. 2). The rock 10a includes a valuable mineral in the form of chalcopyrite and another mineral in the form of quartz, wherein the valuable mineral has a density at least 1.5 times greater than the other mineral.

Starting from a drilling site 1a, a drilling operation is carried out in the rock 10a using a drill 1, wherein drill cuttings 7, 8 including particles 7 of valuable mineral and particles 8 of another mineral are formed. The drill cuttings 7, 8 are removed from drill bit 1b by introducing a gas stream into the drill 1 in the direction of the drill bit 1b. From the drill cuttings 7, 8 and the gas stream, a flowable aerosol 4 is formed which is conveyed counter to the drilling direction to the surface of the ground. The aerosol 4 is now fed from the drill 1 via an aerosol line 4a to an air classifier 5, here in the form of a cross-flow classifier, and hydraulic classification is carried out in a gas flow 9, wherein the drill cuttings 7, 8 are split into at least two, in this example three fractions 6a, 6b, 6c. However, the drill cuttings can also be broken down into more fractions. Each fraction 6a, 6b, 6c comprises equal-settling particles of the drill cuttings 7, 8, i.e. the fraction 6c, for example, includes both small particles 7' of valuable mineral and much larger particles 8' of the other mineral of lower density which are carried away equally far by the gas flow 9 because of the equal settling rate.

Particle size analysis is now carried out on all three fractions 6a, 6b, 6c. This can take place sequentially, but is preferably performed simultaneously for all the fractions 6a, 6b, 6c trickling out of the discharge chutes 5a, 5b, 5c of the air classifier 5. The precise sequence is shown by way of example for the fraction 6c emerging from the discharge chute 5c of the air classifier 5. A frequency h of particles of each particle size d or more specifically particle diameter is determined. Two particle fractions 7a, 8a having different average particle sizes $d_{m1}$, $d_{m2}$ are produced which are here separated from one another by a gap grading. A gap grading is to be understood here as meaning a region in which no particles are present for particular particle sizes.

The particle size analysis is now further evaluated for the fraction in which the gap between the two particle fractions is at a maximum. Consequently, the gap grading region is here particularly large. Here it will now be assumed that the fraction 6c fulfills this condition.

The particle size d of the first particle fraction 7a of the fraction 6c is now used as a measure for the local mineral grain size of the valuable mineral in the rock 10a. The particle sizes d of the first particle fractions 7a are proportional to the mineral grain size of the valuable mineral in the rock 10a.

A deposit model 100 is now created on the basis of the determined local mineral grain size for each drilling site and depth of the drill bit in the rock. If the mineral grain sizes of the valuable mineral at different depths have been determined at a sufficient number of drilling sites, the deposit model 100 shows a sufficiently good three-dimensional mapping of the deposit, indicating the spatial locations 50, 60, 70, 80, 90 of rock having different local mineral grain sizes of the valuable mineral. Starting from the drilling site 1a, here five different mineral grain sizes for the valuable mineral have therefore been determined vertically depth-wise.

FIG. 2 schematically illustrates an apparatus for performing the method in the region of a deposit 10 comprising rock 10a shown in cross-section. The apparatus comprises a drill 1 having a drill bit 1b and a unit 2 for providing the gas stream for forming the aerosol 4, which unit is connected to the drill 1 via at least one gas line 3. The apparatus additionally comprises an air classifier 5 which is connected to the drill 1 via an aerosol line 4a.

In order to perform hydraulic classification of the drill cuttings 7, 8, the air classifier 5 in this example is supplied with the gas flow 9 by the unit 2 via another gas line 3' (see FIG. 1). The apparatus additionally comprises a device 11 for performing particle size analyses on the equal-settling particles of the fractions 6a, 6b, 6c, and a processor unit 12 connected thereto via a data link but set up physically separated from the drilling operation. The device 11 here performs optical analysis, in particular by means of laser diffraction, and is installed downstream of the respective discharge chute 5a, 5b, 5c of the air classifier 5 for the fractions 6a, 6b, 6c, where the fractions 6a, 6b, 6c are in free fall. Alternatively and preferably, there are as many devices 11 as discharge chutes 5a, 5b, 5c, one being installed for each discharge chute 5a, 5b, 5d of the air classifier 5, in order to simultaneously perform particle size analysis for each of the fractions 6a, 6b, 6c.

The particle size analyses determined by the at least one device 11 can either be evaluated in the device 11 and the evaluation transmitted to the processor unit 12, or evaluated by the processor unit 12 itself. For the evaluation, the particle fractions of each fraction 6a, 6b, 6c are analyzed and the fraction having the maximum gap between the first particle fraction 7a and the second particle fraction 7b is selected. The first particle fraction 7a of this selected fraction 6a, 6b, 6c is used for determining the local mineral grain size of the valuable mineral in the rock 10a, as a correlation between them exists.

In order to be able to record the drilling position of the drill 1 in the deposit or occurrence 10, the drill 1 has at least one GPS unit 14. The position data, in particular the current depth of the drill bit 1b and at least one measured value characterizing the drilling behavior, such as the drilling rate, for example, are transmitted in particular by radio 15 to the processor unit 12 disposed physically separated from the drilling operation.

On the basis of the data now available, a deposit model 100, i.e. a model of an occurrence, is created using the processor unit 12.

Also preferably installed on the drill 1 is a structure-borne noise sensor 13 which is used for acquiring another measured value characterizing the current drilling behavior, here the vibration behavior of the drill pipe 1c of the drill 1. With knowledge of the drilling parameters predefined at the drill 1 and of the vibration behavior of the drill pipe 1c, a dependence of the vibration behavior on the drilling parameters can be computationally eliminated using an additional processor unit 12a which is disposed in physical proximity to the drill 1. A rock texture dependent characteristic value is produced which can be additionally used as another measure for determining the local mineral grain size of the valuable mineral and also in particular the hardness of the rock. The vibration behavior data is usually so extensive that radio transmission of said data to the processor unit 12 is difficult to implement. However, vibration data evaluation carried out in the locally installed additional processor unit 12a can be transmitted by radio from the additional processor unit 12a to the remotely disposed processor unit 12.

Figure 3:
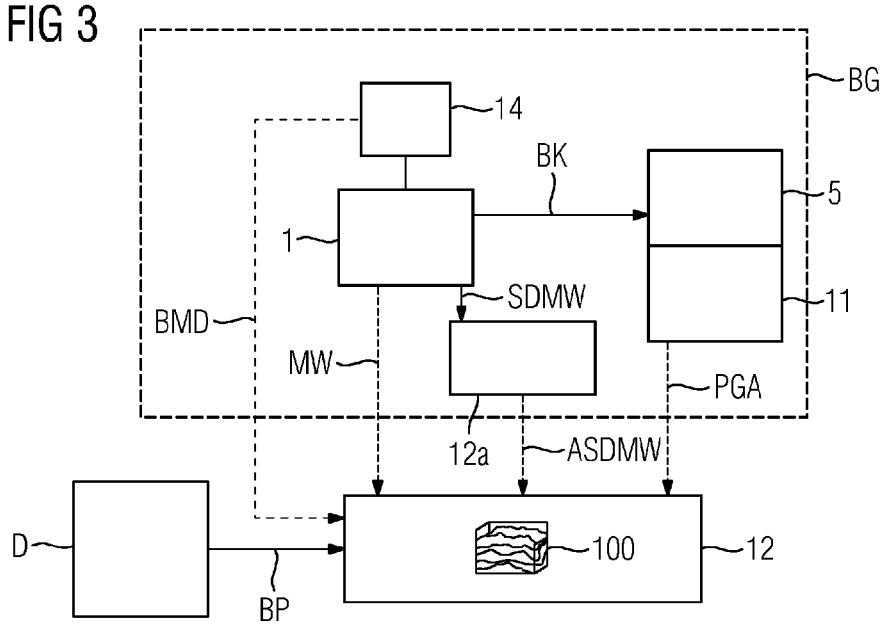

FIG. 3 schematically illustrates the main data and material flows for a possible method. The processor unit 12 is supplied via a data source D with the generally known drilling parameters BP, the data source possibly being operating personnel and/or other electronic devices. Drilling parameters BP are transmitted in the form of data concerning the type of drill 1, the type and geometry of the drill bit of the drill 1, the length of time for which the drill bit has already been operated, the pressure and/or speed of the drill bit, etc. A wireline data link is generally employed. During the drilling operation, current measured values MW characterizing the drilling behavior are transmitted from the drill 1, or more specifically measuring sensors present thereon, to the processor unit 12. Said measured values MW are, for example, a drilling rate, an energy input to the drill 1, etc. In addition, the current position data BMD of the drill 1, in particular of the drill bit, is transmitted to the processor unit 12 by the at least one GPS unit 14.

After formation of the aerosol, the cuttings BK produced by the drill are conveyed to the air classifier 5 and hydraulically classified. The fractions emerging from the discharge chutes of the air classifier 5 are each analyzed by the at least one device 11 in respect of the particle size distribution present therein. The determined analysis data PGA is transmitted, possibly after further evaluation in the device 11 in respect of the fraction having the largest gap grading, to the processor unit 12.

When the measured values MW, the position data BMD and the particle size analysis PGA in the region of the drilling operation BG have been recorded, these are preferably transmitted wirelessly 15 (see dashed lines) to the processor unit 12 disposed physically separated therefrom.

Measured values MW for the drilling behavior, which are available in the form of vibration data SDMW, are transmitted over a wireline connection 15a to the other processor unit 12a where they are evaluated directly in the region of the drilling operation BG and then transmitted wirelessly 15 to the processor unit 12.

The model 100 determined in the processor unit provides in particular a basis for controlling the extraction operation in the region of the deposit or occurrence, especially in respect of blasting, transportation and storage of the extracted rock and also of rock comminution. Thus, with knowledge of the model 100 and possibly of the local hardness of the rock, the locally used amount of explosive can be adjusted, and the extracted rock can be stored at different locations or comminuted in differing degrees depending on the quality.

FIGS. 1 to 3 merely show examples of the method and the apparatus. A person skilled in the art will be readily able to adapt the disclosed apparatus and method to suit the respective deposit or the respective occurrence in order to determine the local mineral grain sizes of the valuable minerals present.

Thus, for example, the soil can of course also be drilled into vertically and/or horizontally and/or obliquely depending on the deposit or occurrence. In addition, some other kind of air classifier and/or device for performing the determination of a property of the selected fraction can be used. Thus, for example, the hydraulically classified fractions can be screen-graded into particle fractions, although this is more time-consuming than optical analysis of the particle sizes.

What is claimed is:

1. A method for determining a local mineral grain size of a valuable mineral in a rock that comprises at least one other mineral having a lower density than the valuable mineral, the method comprising:
- performing a drilling operation in the rock using a drill, wherein the drilling operation produces drill cuttings,
- forming an aerosol comprising the drill cuttings and a gas stream,
- conveying the aerosol from the drill to at least one air classifier,
- performing hydraulic classification to form at least two fractions each comprising equal-settling particles of the drill cuttings, and
- determining a property of at least one of the fractions, and using the determined property as a measure for a local mineral grain size of the valuable mineral in the rock.

2. The method of claim 1, wherein:
- the property is determined by performing particle size analysis on the equal-settling particles of the fractions,
- at least one of the fractions includes two particle fractions having different average particle sizes which are separated from one another by a gap grading, and
- particle sizes d of a first particle fraction are used as a measure for the local mineral grain size of the valuable mineral in the rock.

3. The method of claim 2, wherein in the case that particle size analyses of at least two fractions each show a gap grading, the first particle fraction is used as a measure for the local mineral grain size of the valuable mineral in the rock, which particle fraction is selected as the fraction having the largest gap grading.

4. The method of claim 1, wherein the local mineral grain size of an ore mineral is determined.

5. The method of claim 2, wherein particle size analysis is performed automatically by optical analysis.

6. The method of claim 2, wherein particle size analysis of the equal-settling particles of the fractions is performed continuously during the fall thereof.

7. The method of claim 1, wherein, during the drilling operation, a depth of a drill bit of the drill and/or position data relating to a position of the drill bit are recorded and logically linked with the measure associated with this location, and wherein a three-dimensional mineral grain size distribution of the valuable mineral is determined therefrom.

8. The method of claim 1, comprising:
recording on the drill at least one predefined drilling parameter and at least one measured value characterizing a current drilling behavior of the drill are recorded,
computationally eliminating a dependence of the at least one measured value on the at least one drilling parameter, and
using at least one resulting rock texture dependent characteristic value as another measure for determining the local mineral grain size of the valuable mineral.

9. The method of claim 8, wherein that the at least one drilling parameter is constituted by at least one of: a pressure of the drill bit of the drill, a rotational speed of the drill bit, a flow rate of the gas stream for forming the aerosol, an impact frequency of the drill bit, a previous period of use of the drill bit and, material or geometry data of the drill bit.

10. The method of claim 8, wherein the at least one measured value characterizing the current drilling behavior is selected from the group of measured values consisting of the drilling rate, a resulting torque on the top drive of the drill bit, a gas pressure of the gas stream for forming the aerosol, an energy input to the drill, and a vibration behavior of a drill pipe of the drill.

11. An apparatus for determining a local mineral grain size of a valuable mineral in a rock that comprises at least one other mineral having a lower density than the valuable mineral, the apparatus comprising:
a drill configured to perform a drilling operation in the rock, wherein the operation produces drill cuttings,
a unit for providing a gas stream for forming an aerosol comprising the drill cuttings, the unit being connected to the drill via at least one gas line,
an air classifier connected to the drill via at least one aerosol line, the air classifier being configured to perform a hydraulic classification to form at least two fractions each comprising equal-settling particles of the drill cuttings,
at least one device for determining a property of at least one of the fractions, and
at least one processor unit connected to the at least one device by a data link and configured to record the determined property and correlate it with a local mineral grain size of the valuable mineral in the rock.

12. The apparatus of claim 11, wherein the at least one device is configured to perform particle size analysis, and wherein the at least one device or the at least one processor unit is used to correlate the first particle fraction with the local mineral grain size of the valuable mineral in the rock.

13. The apparatus of claim 11, wherein the at least one processor unit is additionally used to record, at the drill, the at least one drilling parameter or the at least one measured value characterizing the current drilling behavior of the drill.

14. The apparatus of claim 11, wherein the at least one processor unit is additionally configured to computationally eliminate a dependence of the at least one measured value characterizing the current drilling behavior of the drill on the at least one drilling parameter and calculate the at least one rock texture dependent characteristic value which constitutes another measure for at least one of the local mineral grain size of the valuable mineral and a hardness of the rock.

15. The apparatus of claim 14, wherein the at least one processor unit is additionally configured to determine the local mineral grain size of the valuable mineral on the basis of the measure and the additional measure.

16. The apparatus of claim 11, wherein the at least one air classifier and the at least one device for performing particle size analysis, are disposed on the drill.

17. The apparatus of claim 11, wherein there is provided on the at least one drill at least one structure-borne noise sensor for detecting a vibration behavior of the drill pipe of the drill.

\* \* \* \* \*